(12) United States Patent
Shinada et al.

(10) Patent No.: US 8,773,138 B2
(45) Date of Patent: Jul. 8, 2014

(54) DISCHARGE IONIZATION CURRENT DETECTOR

(75) Inventors: Kei Shinada, Uji (JP); Shigeyoshi Horiike, Uji (JP); Takahiro Nishimoto, Soraku-gun (JP)

(73) Assignee: Shimadzu Corporation, Kyoto-Shi (JP)

( * ) Notice: Subject to any disclaimer, the term of this patent is extended or adjusted under 35 U.S.C. 154(b) by 498 days.

(21) Appl. No.: 13/167,634

(22) Filed: Jun. 23, 2011

(65) Prior Publication Data

US 2011/0316552 A1    Dec. 29, 2011

(30) Foreign Application Priority Data

Jun. 28, 2010  (JP) ................................. 2010-145876

(51) Int. Cl.
*G01N 27/62*    (2006.01)

(52) U.S. Cl.
USPC ...... 324/464; 250/287; 250/288; 250/339.03; 250/374; 73/31.05; 324/459; 324/460; 324/465

(58) Field of Classification Search
CPC ....... G01N 27/70; G01N 27/68; G01N 27/66; G01N 27/62; G01N 27/626; G01N 30/60; G01N 30/64; G01N 30/70; G01N 30/78; G01N 30/466
USPC ............. 324/464; 250/287–288, 339.03, 374; 73/31.05
See application file for complete search history.

(56) References Cited

U.S. PATENT DOCUMENTS

| 5,394,092 A | | 2/1995 | Wentworth et al. ........... 324/464 |
| 5,594,346 A | * | 1/1997 | Stearns et al. ................ 324/464 |
| 5,892,364 A | * | 4/1999 | Monagle ....................... 324/464 |

FOREIGN PATENT DOCUMENTS

| JP | 2010-060354 | 3/2010 |
| WO | WO 2009/119050 A1 | 10/2009 |

OTHER PUBLICATIONS

Chinese Office Action dated Jul. 23, 2013 for corresponding Chinese Patent App. No. 201110179412.2.
English translation of "Reason for Rejection" in Chinese Office Action dated Jul. 23, 2013 for corresponding Chinese Patent App. 201110179412.2.

* cited by examiner

*Primary Examiner* — Arleen M Vazquez
*Assistant Examiner* — Son Le
(74) *Attorney, Agent, or Firm* — Bingham McCutchen LLP

(57) ABSTRACT

A discharge ionization current detector using a low-frequency barrier discharge is provided to improve the linearity of detection sensitivity with respect to a sample introduction amount. From a lower end of a lower gas passage connected to a lower end of an upper gas passage, a dilution gas is supplied upward against a downward flow of a plasma gas. A gas discharge passage for discharging a plasma gas, the dilution gas and a sample gas is arranged between an ion-collecting electrode and a bias voltage application electrode. The sample gas introduced through a capillary tube is mixed with the plasma gas and the dilution gas due to a disturbed flow generated by collision of the plasma gas and the dilution gas. The sample component is efficiently ionized by light from the plasma without undergoing light-shielding effect of concentrated sample components.

3 Claims, 3 Drawing Sheets

DISCHARGE IONIZATION CURRENT DETECTOR

TECHNICAL FIELD

The present invention relates to a discharge ionization current detector primarily suitable as a detector for a gas chromatograph (GC), and more specifically to a discharge ionization current detector using a low-frequency barrier discharge.

BACKGROUND ART

As a detector for a gas chromatograph, various types of detectors have been practically applied, such as a thermal conductivity detector (TCD), electron capture detector (ECD), flame ionization detector (FID), flame photometric detector (FPD), and flame thermionic detector (FTD). Among these detectors, the FID is most widely used, particularly for the purpose of detecting organic substances. The FID is a device that ionizes sample components in a sample gas by hydrogen flame and detects the resultant ion current. It can attain a wide dynamic range of approximately six orders of magnitude. However, the FID has the following drawbacks: (1) Its ionization efficiency is low, so that its minimum detectable amount is not sufficiently low. (2) Its ionization efficiency for alcohols, aromatic substances, and chlorine substances is low. (3) It requires hydrogen, which is a highly hazardous substance; therefore, an explosion-proof apparatus or similar kind of special equipment must be provided, which makes the entire system more difficult to operate.

On the other hand, as a detector capable of high-sensitivity detection of various compounds from inorganic substances to low-boiling organic compounds, a pulsed discharge detector (PDD) has conventionally been known (for example, refer to Patent Document 1). In the PDD, the molecules of helium or another substance are excited by a high-voltage pulsed discharge. When those molecules return from their excited state to the ground state, they generate optical energy. This optical energy is utilized to ionize a molecule to be analyzed, and an ion current produced by the generated ions is detected to obtain a detection signal corresponding to the amount (concentration) of the molecule to be analyzed.

In most cases, the PDD can attain higher ionization efficiencies than the FID. For example, the ionization efficiency of the FID for propane is no higher than 0.0005%, whereas the PDD can achieve a level as high as 0.07%. Despite this advantage, the dynamic range of the PDD is not as wide as that of the FID; the fact is that the former is lower than the latter by one or more orders of magnitude. This is one of the reasons why the PDD is not as widely used as the FID.

The most probable constraining factors for the dynamic range of the conventional PDD are the unstableness of the plasma created for the ionization and the periodic fluctuation of the plasma state. To solve this problem, a discharge ionization current detector has been proposed (for example, refer to Patent Document 2). This detector uses a low-frequency AC-excited dielectric barrier discharge (which is hereinafter referred to as the "low-frequency barrier discharge") to create a stable and steady state of plasma. The plasma created by the low-frequency barrier discharge is non-equilibrium atmospheric pressure plasma, which does not become hot as easily as the plasma created by the radio-frequency discharge. Furthermore, the periodic fluctuation of the plasma, which occurs due to the transition of the voltage application state if the plasma is created by the pulsed high-voltage excitation, is prevented, so that a stable and steady state of plasma can be easily obtained. Based on these findings, the present inventors have conducted various kinds of research on the discharge ionization current detector using a low-frequency barrier discharge and have made many proposals on this technique (for example, refer to Patent Documents 3 and 4).

As described previously, the low-frequency barrier discharge creates a stable plasma state and is also advantageous for noise reduction. Therefore, the discharge ionization current detector using the low-frequency barrier discharge can attain a high SN ratio. However, the conventional discharge ionization current detector using the low-frequency barrier discharge also has problems one of which is poor linearity of detection sensitivity.

FIG. 3 is a graph showing an example of actually measured values of the detection sensitivity in the FID and a conventional general-type discharge ionization current detector when octane ($C_8H_{18}$) is measured. In FIG. 3, the horizontal axis indicates a logarithmic value of a sample introduction amount, while the vertical axes indicate the detection sensitivity. In the vertical axes, the left-hand axis indicates a scale for the FID while the right-hand axis indicates a scale for the discharge ionization current detector. As for the discharge ionization current detector, it can be recognized that the absolute value of the detection sensitivity is higher than that for the FID by approximately two orders of magnitude, while the range where the linearity of the sensitivity with respect to the sample introduction amount is maintained is narrower than that for the FID. The sensitivity remarkably decreases particularly in an area where the sample concentration is high. Although not shown in FIG. 3, the linearity of the sensitivity is practically kept in the area lower than 0.01 ng for the FID. In the FID, the linearity of the sensitivity is kept over a range of approximately seven orders of magnitude of the sample introduction amount. On the other hand, the linearity of the sensitivity is kept over a range no wider than four orders of magnitude of the sample introduction amount for the discharge ionization current detector.

BACKGROUND ART DOCUMENT

Patent Document

Patent Document 1: U.S. Pat. No. 5,394,092 A1
Patent Document 2: U.S. Pat. No. 5,892,364 A1
Patent Document 3: WO-A1 2009/119050
Patent Document 4: JP-A 2010-60354

DISCLOSURE OF THE INVENTION

Problem to be Solved by the Invention

The present invention is made to solve the previously described problems, and a primary purpose thereof is to broaden a sample introduction amount range in which the linearity of detection sensitivity can be kept in a discharge ionization current detector using a low-frequency barrier discharge.

Means for Solving the Problems

In a discharge ionization current detector using a low-frequency dielectric barrier discharge, a sample component is primarily ionized by an action of light from plasma, and in a conventional configuration, the detection sensitivity remarkably decreases particularly when the concentration of the sample components is high. Accordingly, one of the reasons for the decrease in the detection sensitivity in the conventional configuration is probably because only a part of the sample components is sufficiently irradiated with light because of the influence of the absorption or scattering of light due to high-concentrated sample components, so that the ionization efficiency cannot be high. Furthermore, according to a study by the present inventors, it is highly possible that, even if a sufficient amount of ions are created, a long movement distance of ions to an ion-collecting electrode may cause the ions to disappear halfway since the lifetime of the created ions is very short. In addition, the created ions move to an ion-collecting electrode by action of an electric field formed by a direct current voltage applied to a bias voltage application electrode. However, if the electric field does not sufficiently cover an ion generation area, the moving speed of the ions becomes low, thereby eventually causing the ions to disappear along the way of moving.

In view of the previously described points, the present inventors have conceived the idea of improving the linearity of sensitivity with respect to a sample introduction amount by efficiently and quickly spreading the sample components to an area out of the range of influence of absorption and scattering of light due to the high-concentration sample components, after introduction of a sample gas into a gas passage, and minimizing the distance between the area where the sample component is ionized and the ion-collecting electrode or the bias voltage application electrode, each adopted to detect ion current. The present inventors have also experimentally confirmed the effect obtained by the improvement.

Specifically, the present invention made to solve the previously described problems relates to a discharge ionization current detector for ionizing and detecting a sample component in a sample gas where the sample gas is ionized using plasma created by discharge. The discharge ionization current detector includes:

a) a plasma generation means causing a dielectric barrier discharge to be created by a low-frequency AC electric field in a first gas passage in which a plasma gas flows in one direction, so as to create a plasma from the plasma gas by the discharge;

b) a second gas passage connected to an outlet end of the first gas passage, in which a dilution gas is caused to flow from an end opposed to the connection to the first gas passage in a direction opposite to a flow of the plasma gas;

c) a sample gas introduction passage for introducing a sample gas into the second gas passage;

d) an ion current detection means including an ion-collecting electrode and a bias voltage application electrode located apart from each other in a direction of the gas flow in the second gas passage, for detecting an ion current originating from the sample component in the sample gas ionized by an action of the plasma created by the plasma generation means; and e) a gas discharge passage connected to the second gas passage with an inlet end located between the ion-collecting electrode and the bias voltage application electrode, for discharging the plasma gas, the dilution gas and the sample gas from the second gas passage to an outside.

As a preferable embodiment of the discharge ionization current detector according to the present invention, the ion-collecting electrode and the bias voltage application electrode are arranged in this order in the flowing direction of the plasma gas, and the sample gas introduction passage is arranged to introduce the sample gas into a space on a side where the ion-collecting electrode is positioned, in relation to the connection portion of the gas discharge passage in the second gas passage.

Any type of gas selected from helium, argon, nitrogen, neon and xenon as well as any mixture thereof can be used as the plasma gas or dilution gas.

In the discharge ionization current detector according to the present invention, the plasma-gas flow and the dilution-gas flow collide with each other around the connection portion at the inlet end of the gas discharge passage in the second gas passage, and flow into the gas discharge passage, creating a large disturbed flow. The disturbed flow generated in the second gas passage allows sample components, included in the sample gas introduced through the sample gas introduction passage, to be quickly spread in the plasma gas or the dilution gas. Accordingly, if sample components having relatively-high concentration exist around the outlet end of the sample gas introduction passage, a sufficient amount of light irradiates the sample components that have spread in an area free from the light-shielding effect of the high-concentration components. As a result, the sample components can be ionized with high efficiency.

Around the inlet end of the gas discharge passage in the second gas passage, the plasma gas and the dilution gas exist in a condition that both gasses are sufficiently mixed with sample components. Accordingly, ions originating from the sample components are created in an area near the inlet end of the gas discharge passage in the second gas passage. This area is sandwiched between the ion-collecting electrode and the bias voltage application electrode and close to both electrodes. Accordingly, a sufficiently large electric field acts in the area, causing the ions to quickly move toward the ion-collecting electrode. Furthermore, since the movement distance of the ions is short, the ions arrive at the ion-collecting electrode in a short period of time before the ions come to the end of their lifetime and disappear. Accordingly, the ions can be efficiently introduced to the ion-collecting electrode, to thereby be reflected in the ion current.

Effect of the Invention

The discharge ionization current detector of the present invention can achieve high ionization efficiency and high ion collection efficiency, and thereby maintain detection sensitivity even in the case where the concentration of the sample components is so high that the detection sensitivity would remarkably decrease if a conventional configuration was used. Therefore, the linearity of the detection sensitivity with respect to the sample introduction amount improves in comparison with the conventional configuration, so that sample components can be detected over a broad range of concentrations.

BEST MODE FOR CARRYING OUT THE INVENTION

Figure 1:
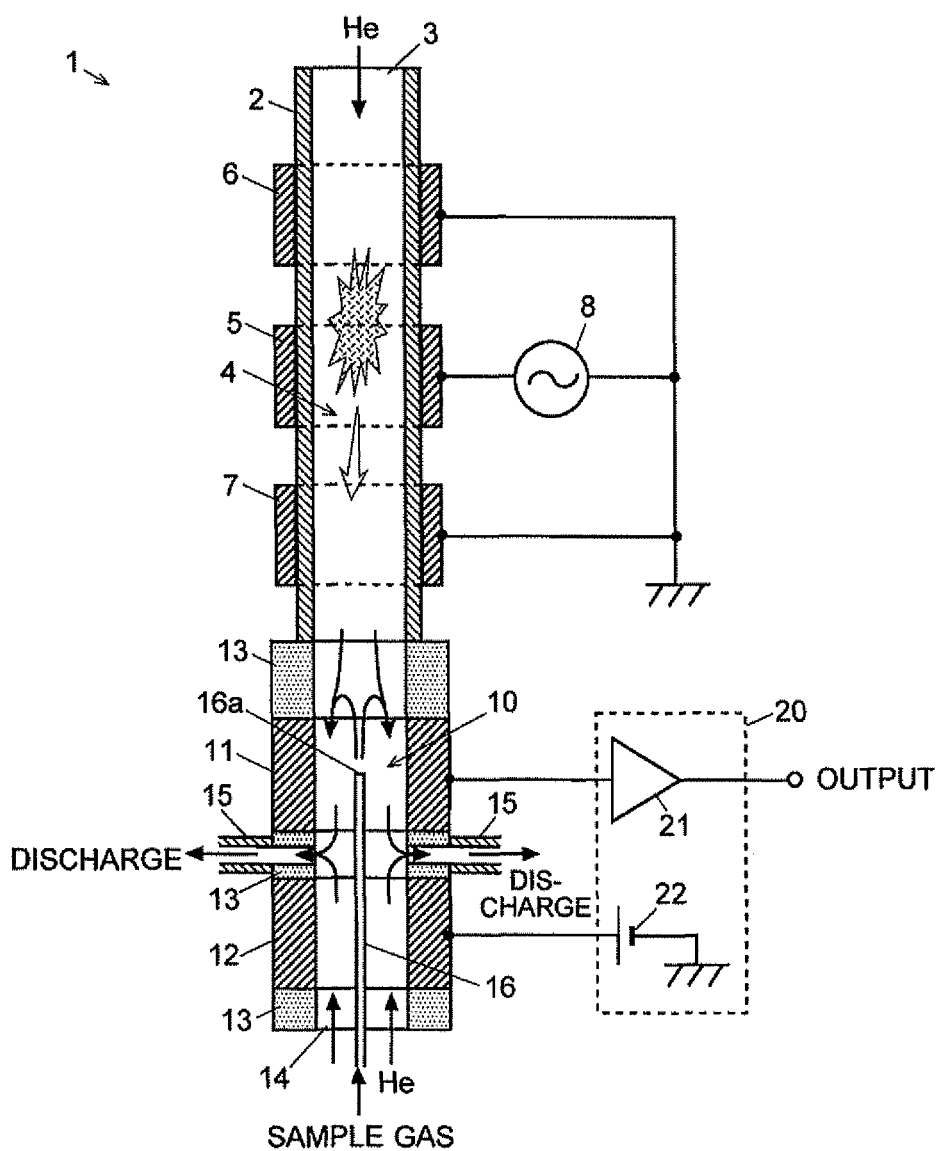
FIG. 1 is a schematic configuration diagram showing a discharge ionization current detector according to an embodiment of the present invention.

A discharge ionization current detector according to an embodiment of the present invention is described with reference to the attached drawings. FIG. 1 is a schematic configuration diagram showing the discharge ionization current detector according to the present embodiment.

A discharge ionization current detector 1 of the present embodiment includes a cylindrical tube 2 which is a quartz tube having an outer diameter of 3.9 mm. The inner space of the cylindrical tube 2 is an upper gas passage 4 having an upper end portion serving as a plasma gas introduction port 3. It should be noted that the material of the cylindrical tube 2 does not need to be quartz as long as it is a dielectric material. Ring-shaped plasma generation electrodes 5, 6 and 7, which are made of a metal (e.g. stainless steel or copper), are circumferentially provided at predetermined intervals on the outer wall surface of the cylindrical tube 2 along the longitudinal direction thereof. According to this design, the dielectric wall of the cylindrical tube 2 between the gas passage 4 and the plasma generation electrodes 5, 6 and 7 functions as a dielectric coating layer that covers the electrodes 5, 6 and 7, thereby enabling dielectric barrier discharge to occur.

Among the three plasma generation electrodes 5, 6 and 7, the central electrode 5 is connected to an excitation high-voltage power source 8, while the other electrodes 6 and 7 located on both sides of the central electrode 5 are connected to a ground. The structure in which the electrode 5, to which the high voltage is applied, is sandwiched between the grounded electrodes 6 and 7 prevents the plasma produced by the electric discharge from spreading toward the upstream and downstream ends of the gas stream, thereby limiting the substantial plasma generation area to the space between the two plasma generation electrodes 6 and 7.

The excitation high-voltage power source 8 generates a low-frequency high AC voltage. Its frequency is within the range from 50 Hz to 100 kHz, and more preferably from 100 Hz to 20 kHz. The AC voltage may have any waveform, such as sine waves, rectangular waves, triangular waves or sawtooth waves.

An ion-collecting electrode 11 and a bias voltage application electrode 12 are arranged in the lower portion of the cylindrical tube 2, with each electrode being sandwiched by insulators 13 made of alumina, PTFE resin or other materials. These electrodes each consist of a cylindrical body having the same inner diameter. These cylindrical bodies internally define a lower gas passage 10 continuously extending from an upper gas passage 4. The lower end of the lower gas passage 10 is a dilution gas introduction port 14 from which a capillary tube 16 for introducing a sample gas is inserted in the lower gas passage 10. The central axis of the capillary tube 16 is almost identical to that of the lower gas passage 10. The distal end of the capillary tube 16 is disposed in a region surrounded by the ion-collecting electrode 11. The insulator 13 sandwiched between the ion collecting-electrode 11 and the bias voltage application electrode 12 is connected with gas discharge tubes 15 at two portions facing each other across the central axis of the lower gas passage 10.

An ion current detector 20 for detecting an ion current includes a current amplifier 21 and a bias direct-current power source 22. The bias direct-current power source 22 applies a predetermined direct-current bias voltage to the bias voltage application electrode 12. An input end of the current amplifier 21 is connected to the ion-collecting electrode 11. The current amplifier 21 detects and amplifies the current flowing due to ions arriving at the ion-collecting electrode 11.

Figure 2A:
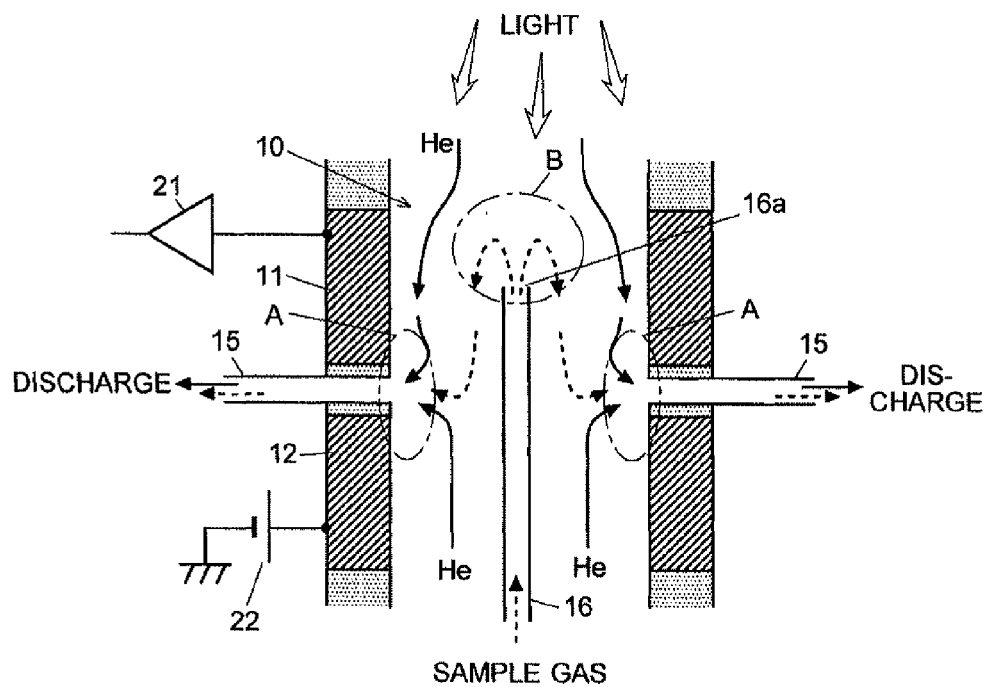
FIGS. 2A and 2B are configuration diagrams showing the main parts of the discharge ionization current detector of the present embodiment for describing a detection operation thereof in comparison with a conventional configuration.
Figure 2B:
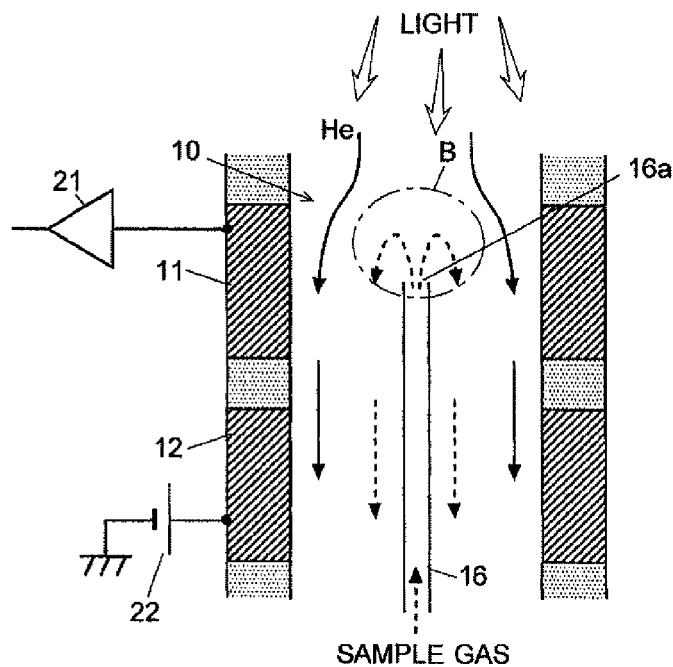
Figure 3:
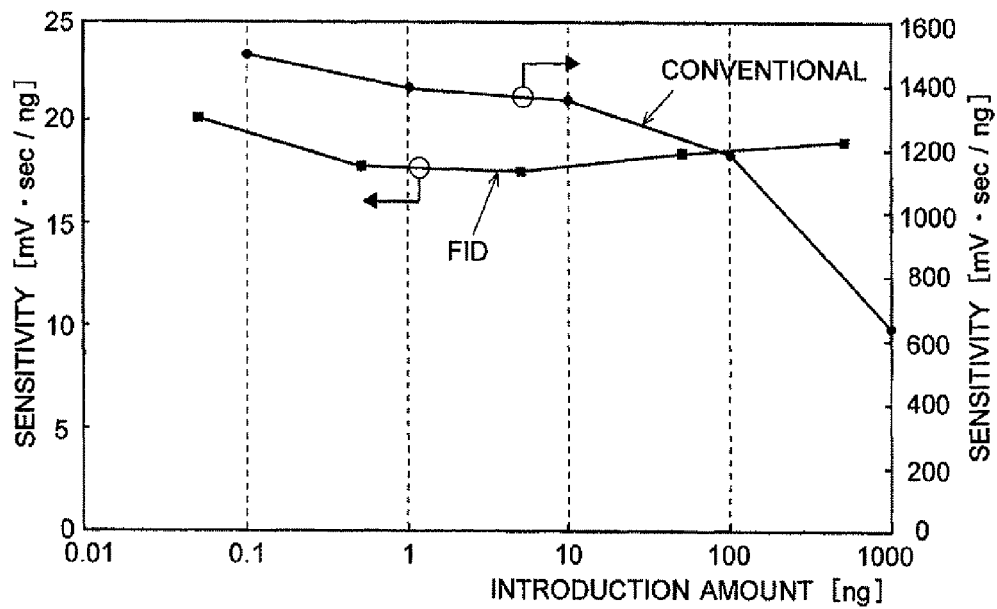
FIG. 3 shows examples of actually measured values of the detection sensitivity in a FID and a conventional general-type discharge ionization current detector when octane is measured.

Next, a detection operation of the discharge ionization current detector 1 is described with reference to FIGS. 2A and 2B in addition to FIG. 1. FIG. 2A is a partially-enlarged diagram showing the inner space of the lower gas passage 10 for describing the detection operation of the discharge ionization current detector according to the present embodiment. FIG. 2B is also a partially-enlarged diagram of a conventional discharge ionization current detector to be compared, showing the same portion as shown in FIG. 2A.

As indicated by the downward-pointing arrow in FIG. 1, a predetermined flow rate of helium (He), which serves as the plasma gas, is supplied into a plasma gas supply port 3. Furthermore, as indicated by the upward-pointing arrows in FIG. 1, the same helium as supplied from the plasma gas supply port 3 is supplied as a dilution gas with the same flow rate from a dilution gas supply port 14. Furthermore, as indicated by the upward-pointing broken-line arrow in FIG. 2A, a sample gas which contains components to be detected is supplied into the capillary tube 16. For example, when the present detector is used as a detector for a gas chromatograph, a sample gas that has been separated into components by a column may be introduced in the capillary tube 16. The plasma gas or the dilution gas is a kind of gas that can be easily ionized, examples of which include helium, argon, nitrogen, neon, xenon and any mixture of two or more of these elements.

The plasma gas flows downward through the upper gas passage 4 to join the sample gas supplied through the capillary tube 16 and be discharged from a gas discharge port 16a, then flows downward to the middle of the lower gas passage 10. Meanwhile, the dilution gas flows upward to the middle of the lower gas passage 10. The gas flowing downward from the upside and the gas flowing upward from the downside collide with each other around the connection portions of the gas discharge tubes 15, to be joined and then eventually discharged through the gas discharge tubes 15.

When the plasma gas flows through the upper gas passage 4 in the previously described manner, a control signal is given from a non-illustrated controller to the excitation high-voltage power source 8, which then applies a low-frequency high AC voltage between the plasma generation electrode 5 and each of the other electrodes 6 and 7. As a result, dielectric barrier discharge induced through the dielectric coating layer (a part of the wall surface of the cylindrical tube 2) occurs between the plasma generation electrode 5 and each of the plasma generation electrodes 6 and 7. Due to this dielectric barrier discharge, the plasma gas flowing through the upper gas passage 4 is ionized in a wide area. Thus, a cloud of plasma (i.e. atmospheric non-equilibrium micro-plasma) is created.

Emission light due to the plasma created by the previously-described discharge passes through the upper gas passage 4 to cover the lower gas passage 10. Sample components in the sample gas discharged into the lower gas passage 10 from the gas discharge port 16a at the distal end of the capillary tube 16 primarily exist in an area between the gas discharge port 16a and the connection portions of the gas discharge tubes 15 in the lower gas passage 10. When the emission light due to the plasma reaches the area where the sample components exist, the sample components are ionized primarily by photoionization. Sample ions created in this manner are attracted to the ion-collecting electrode 11 due to the action of the bias DC voltage at a level of 100 to 200V applied to the bias voltage application electrode 12 so as to receive electrons from, or give electrons to, the ion-collecting electrode 11. Accordingly, an ion current corresponding to the amount of the sample ions created by the ionization, in other words, an ion current corresponding to the amount of the sample components, is inputted to the current amplifier 21. The current amplifier 21 amplifies the ion current so as to output a detection signal. In this manner, the discharge ionization current detector 1 outputs a detection signal corresponding to the amount (concentration) of the sample components in the introduced sample gas.

In a conventional discharge ionization current detector, as shown in FIG. 2B, no gas discharge tube is connected between the ion-collecting electrode 11 and the bias voltage application electrode 12. Accordingly, the gas flows downward in the lower gas passage 10. The sample gas is discharged in a direction opposed to the downward gas flow. However, the flow rate of the sample gas is significantly lower than the flow rate of the plasma gas, Accordingly, the sample gas flows downward around the capillary tube 16, with a large amount of plasma gas flowing downward around the sample gas. As described previously, the sample gas is not completely mixed with the plasma gas and both are separated like a sheath, or the sample gas flows without being completely diluted by the plasma gas. Accordingly, the following problems may occur.

When the concentration of the sample components in the sample gas is high, the sample concentration is particularly high in an area B around the gas discharge port 16a. Therefore, light emitted from the plasma is absorbed and/or scattered in the area B and hence can hardly reach the lower side of the area B. Accordingly, the sample gas flowing along the capillary tube 16 cannot be sufficiently irradiated with the light. As a result, though the sample components in and around the area B are ionized, it is difficult for the sample components in the other areas to be ionized. This makes the ionization efficiency itself difficult to increase. Furthermore, the area B is positioned around the center of the lower gas passage 10 in the radius direction thereof, and hence is comparatively far away from the ion-collecting electrode 11 and the bias voltage application electrode 12. Therefore, the electric potential gradient around the area B created by the electric field formed by the bias voltage application electrode 12 is gradual. Accordingly, sample ions created around the area B are barely accelerated toward the ion-collecting electrode 11. Furthermore, the created ions typically have a short lifetime, while the distance to the ion-collecting electrode 11 for the sample ion is long, causing the ratio of ions which disappear before reaching the ion-collecting electrode 11 to be high. As a result, the collection efficiency of ions created in the area B becomes insufficient. Furthermore, since the sample gas itself forms plasma around the area B, the decrease in the effective bias voltage due to the plasma cannot be disregarded when the sample concentration is high. This additionally impedes the movement of the ions.

In the conventional configuration shown in FIG. 2B, the previously described various factors cause the sensitivity to suddenly decrease, particularly when the sample concentration is high. As a result, the linearity of the sensitivity decreases.

On the other hand, in the discharge ionization current detector according to the present embodiment, as shown in FIG. 2A, the gas discharge tubes 15 are connected between the ion-collecting electrode 11 and the bias voltage application electrode 12, and helium is supplied from both the upper and lower ends of the lower gas passage 10 in opposite directions with approximately equal flow rates. Accordingly, the following effects can be obtained for the ionization of sample components and the collection of created ions.

Since the plasma gas flowing downward along with the sample gas and the dilution gas flowing upward collide with each other around the connection portions of the gas discharge tubes 15, a turbulence of gas occurs around this area, allowing the sample gas, the plasma gas, and the dilution gas to be easily mixed. Accordingly, an amount of gas in which sample components spread exists around the area A, specifically, in the vicinity of the ion-collecting electrode 11 and the bias voltage application electrode 12 and between the two electrodes 11 and 12. When the sample concentration in the sample gas is high, the sample concentration in the area B around the gas discharge port 16a is also high. However, light from the plasma reaches the area A with little being influenced by absorption or scattering of the light in the area B. This increases the ionization efficiency. Furthermore, since the area A is close to the ion-collecting electrode 11 and the bias voltage application electrode 12, the electric field powerfully acts around the area A. Therefore, ions created in the area A are provided with a large amount of kinetic energy. The distance from the area A to the ion-collecting electrode 11 is short, allowing ions created in the area A to arrive at the ion-collecting electrode 11 before the lifetime of the ions terminates, so that the ions can contribute to the ion current. Accordingly, the efficiency of collection of created ions in the ion-collecting electrode 11 becomes high. Therefore, the discharge ionization current detector according to the present embodiment can maintain a high level of detection sensitivity even when the sample concentration is high and the condition is unfavorable for the ionization or the collection of ions particularly. As a result, the linearity of the detection sensitivity with respect to the sample introduction amount can be improved.

Figure 4:
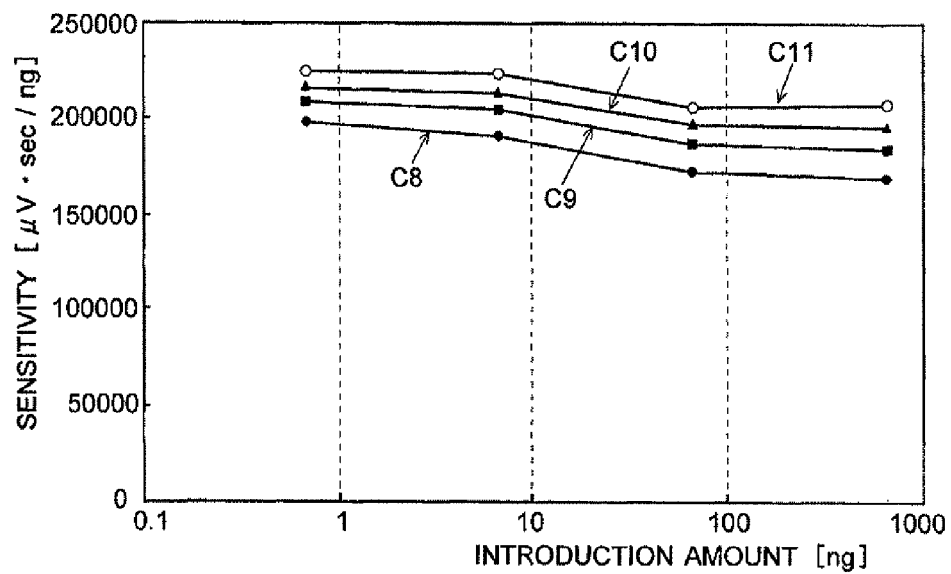
FIG. 4 shows examples of actually measured values of the detection sensitivity in the discharge ionization current detector according to the present embodiment.

FIG. 4 is a graph showing the result of an experiment in which the detection sensitivity of the discharge ionization current detector according to the present embodiment was measured for various samples. The references of C8, C9, C10, and C11 respectively denote octane ($C_8H_{18}$), nonane ($C_9H_{20}$), decane ($C_{10}H_{22}$), and undecane ($C_{11}H_{24}$). Even within the range from 10 to 1000 ng of the sample introduction amount, where the detection sensitivity remarkably decreased in the conventional example, the detection sensitivity was maintained to be comparable to the level obtained within a range equal to or lower than the aforementioned range (10 to 1000 ng) for every sample. Although the absolute value of the sensitivity decreases since the degree of dilution of the sample gas is higher than in the conventional configurations, a sufficiently high sensitivity can be achieved in comparison with a FID or TCD.

It should be noted that the previously described embodiment is a mere example of the present invention. Any change, modification or addition appropriately made within the spirit of the present invention will naturally fall within the scope of claims of the present patent application.

EXPLANATION OF NUMERALS

1 . . . Discharge Ionization Current Detector
2 . . . Cylindrical Tube
3 . . . Plasma Gas Introduction Port
4 . . . Upper Gas Passage
5, 6, 7 . . . Plasma Generation Electrode
8 . . . Excitation High-Voltage Power Source
10 . . . Lower Gas Passage
11 . . . Ion-Collecting Electrode
12 . . . Bias Voltage Application Electrode
13 . . . Insulator
14 . . . Dilution Gas Introduction Port
15 . . . Gas Discharge Tube
16 . . . Capillary Tube

16a ... Gas Discharge Port
20 ... Ion Current Detector
21 ... Current Amplifier
22 ... Bias DC Power Source

The invention claimed is:

1. A discharge ionization current detector for ionizing and detecting a sample component in a sample gas where the sample gas is ionized using plasma created by discharge, comprising:
   a) a plasma generation means causing a dielectric barrier discharge to be created by a low-frequency AC electric field in a first gas passage in which a plasma gas flows in one direction, so as to create a plasma from the plasma gas by the discharge;
   b) a second gas passage connected to an outlet end of the first gas passage, in which a dilution gas is caused to flow from an end opposed to the connection to the first gas passage in a direction opposite to a flow of the plasma gas;
   c) a sample gas introduction passage for introducing a sample gas into the second gas passage;
   d) an ion current detection means including an ion-collecting electrode and a bias voltage application electrode located apart from each other in a direction of the gas flow in the second gas passage, for detecting an ion current originating from the sample component in the sample gas ionized by an action of the plasma created by the plasma generation means; and
   e) a gas discharge passage connected to the second gas passage with an inlet end located between the ion-collecting electrode and the bias voltage application electrode, for discharging the plasma gas, the dilution gas and the sample gas from the second gas passage to an outside.

2. The discharge ionization current detector according to claim 1, wherein the ion-collecting electrode and the bias voltage application electrode are arranged in this order in the flowing direction of the plasma gas, and the sample gas introduction passage is arranged to introduce the sample gas into a space on a side where the ion-collecting electrode is positioned, in relation to the connection portion of the gas discharge passage in the second gas passage.

3. The discharge ionization current detector according to claim 1, wherein the plasma gas and the dilution gas flow at substantially the same flow rate in the second gas passage.

* * * * *